United States Patent [19]
Uchida et al.

[11] Patent Number: 5,503,864
[45] Date of Patent: Apr. 2, 1996

[54] PROCESS FOR PREPARING A FRACTION HAVING A HIGH CONTENT OF α-LACTALBUMIN FROM WHEY AND NUTRITIONAL COMPOSITIONS CONTAINING SUCH FRACTIONS

[75] Inventors: Yukio Uchida, Tokorozawa; Masaharu Shimatani, Sayamashi; Tamami Mitsuhashi, Kawagoe; Masanobu Koutake, Sakado, all of Japan

[73] Assignee: Snow Brand Milk Products, Inc., Hokkaido, Japan

[21] Appl. No.: 284,919

[22] Filed: Aug. 2, 1994

Related U.S. Application Data

[63] Continuation of Ser. No. 18,751, Feb. 17, 1993, abandoned.

[30] Foreign Application Priority Data

Feb. 18, 1992 [JP] Japan ................................. 4-068991

[51] Int. Cl.⁶ .................................................. A23C 21/00
[52] U.S. Cl. .......................... 426/583; 426/657; 530/833
[58] Field of Search .................................. 426/656, 657, 426/583, 478, 580; 530/366, 832, 833

[56] References Cited

U.S. PATENT DOCUMENTS

| | | | |
|---|---|---|---|
| 3,707,770 | 1/1973 | Timmins et al. ........................ | 426/271 |
| 4,018,752 | 4/1977 | Bühler et al. ........................... | 426/656 |
| 4,427,658 | 1/1984 | Maubois et al. ........................ | 424/177 |
| 4,485,040 | 11/1984 | Roger et al. ........................... | 260/122 |
| 4,497,836 | 2/1985 | Mavquandt et al. ..................... | 426/583 |
| 4,518,616 | 5/1985 | Czulak ..................................... | 426/40 |
| 4,699,793 | 10/1987 | Eguchi et al. ........................... | 426/41 |
| 4,711,953 | 12/1987 | Roger et al. ........................... | 530/366 |
| 5,008,376 | 4/1991 | Bottomley .............................. | 530/366 |
| 5,179,197 | 1/1993 | Uchida et al. ........................... | 530/366 |

FOREIGN PATENT DOCUMENTS

| | | | |
|---|---|---|---|
| 2436567 | 5/1980 | France .................................... | 426/583 |
| 7808199 | 2/1980 | Netherlands ........................... | 426/583 |

*Primary Examiner*—Anthony J. Weier
*Attorney, Agent, or Firm*—Testa, Hurwitz & Thibeault

[57] ABSTRACT

A process for producing an α-lactalbumin-enriched fraction from whey is disclosed. The process involves heating pH-adjusted whey to a temperature sufficient to cause aggregation of β-lactoglobulin molecules, and fractioning the whey using ultrafiltration or microfiltration, the α-lactalbumin-enriched fraction obtained by the process is useful for making breast milk substitutes and other nutritional compositions.

16 Claims, 1 Drawing Sheet

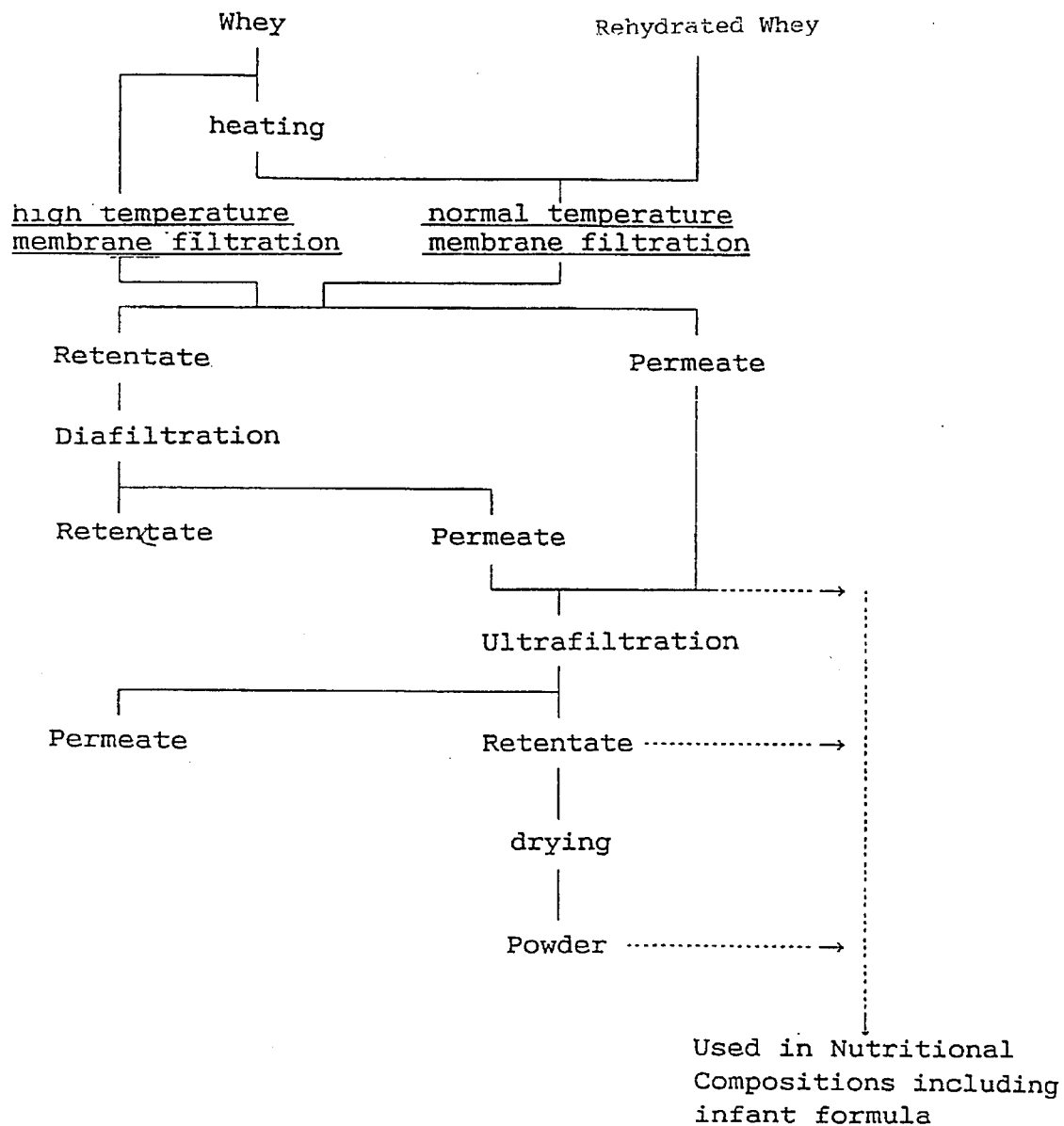

PROCESS FOR PREPARING A FRACTION HAVING A HIGH CONTENT OF α-LACTALBUMIN FROM WHEY AND NUTRITIONAL COMPOSITIONS CONTAINING SUCH FRACTIONS

This is a continuation of application Ser. No. 08/018,751 filed on Feb. 17, 1993 now abandoned.

FIELD OF THE INVENTION

The present invention relates to a process for separating and recovering a fraction having a high content of α-lactalbumin by subjecting whey to membrane filtration.

Furthermore, the present invention relates to a nutritional composition containing such a fraction having a high content of α-lactalbumin thus obtained.

DESCRIPTION OF PRIOR ART

Whey proteins are generally known to be used as a substitute for breast milk and as a protein source in nutritional mixtures both for human and animals since whey protein has a high nutritional value and is also highly efficient in protein utilization, when compared to casein or soya protein. Particularly, when taken as a breast-milk substitute, β-lactoglobulin, the major component of whey protein in cows' milk, acts as an allergen which causes infant allergy since it is a protein not found in breast milk. Therefore, it follows that one should obtain a whey protein source having either a lower β-lactoglobulin content or a higher α-lactalbumin content.

Thus, attempts have hitherto been made to obtain whey protein having either a lower β-lactoglobulin content or a higher α-lactalbumin content and thus achieve a more efficient rate of production from whey, the by-products of cheese production.

As methods for separating and recovering a fraction having high content of α-lactalbumin, there have been proposed numerous attempts to effectively use the difference between the physical and/or chemical properties of various whey proteins with whey as the starting material. In working these methods, however, one encounters various difficulties such as complicated process steps, high energy consumption, poor rates of recovery, irreversible reactions of proteins, which render them impractical for or inoperable as larger scale commercial/industrial processes.

Furthermore, as fractionation methods with ultrafiltration membranes applicants are aware of Peter Harris (U.S. Pat. Nos. 4,485,040 and 4,711,953) and Bottomley (U.S. Pat. No. 5,008,376). In considering these methods, particularly Bottomley, there is observed a considerable variation in the pore sizes of the industrial ultrafiltration membranes employed, which render them impractical to effectively and reliably separate α-lactalbumin (m. W. 14,000 daltons) and β-lactoglobulin (m. W. 36,000 as dimers) which have rather close molecular weights. In Bottomley's examples, the maximum ratio of α-lactalbumin to β-lactoglobulin in the products obtained failed to reach a factor of 3.

As seen in the foregoing paragraphs, conventional methods have been either too complicated with their industrial processes or quite unsatisfactory with the rate of recovery for α-lactalbumin in the fractions obtained. The inventors have therefore arrived at the conclusion that conventional methods fail to show a process sufficiently efficient to separate and recover a fraction having a high content of a-lactalbumin from whey.

SUMMARY OF THE INVENTION

As given above, where α-lactalbumin containing fraction is obtained from whey according to conventional methods, there have been numerous difficulties such as complicated process steps, high energy consumption, poor rate of recovery, undesirable and irreversible reactions with protein, etc., that is, one can only arrive at the conclusion that a method to obtain from whey a fraction having a high content of α-lactalbumin has not been established. It is an object of this invention to obtain from whey, a fraction having a high content of α-lactalbumin at a commercially viable rate of recovery.

It is a further object of this invention to provide a method to separate and recover from whey a fraction having a high content of α-lactalbumin in a commercially viable scale, at low cost and high efficiency.

Another object of this invention is to provide a nutritional composition comprising a fraction having a high content of α-lactalbumin obtained from whey.

The nutritional composition of the present invention includes breast-milk substitutes such as powdered infants' formula, and the like, material for pharmaceutical preparations, nutritional mixtures for humans or animals.

In the present invention, the heating of whey promotes the aggregation of β-lactoglobulin, thus increasing the apparent molecular weight, which is then subject to membrane filtration, a simple operation, thereby fractionating α-lactalbumin against β-lactoglobulin, and thus most reliably performing a highly effective fractionation on the basis of commercial scale production. Also, the present invention relates to obtaining a nutritional composition containing such fraction with a high α-lactalbumin content.

The present invention is directed to a process wherein whey, maintained at pH 4.0–7.5, is first heated or simultaneous with the heating step, is subjected to filtration with an ultrafiltration membrane having a cut-off molecular weight of higher than 50,000, Da, or with a microfiltration membrane having a pore size of smaller than 0.5 um, and then separating and recovering the whey fraction abundant in α-lactalbumin.

The present invention also relates to nutritional compositions containing a fraction obtained as above having a high α-lactalbumin content.

BRIEF DESCRIPTION OF THE FIGURE

The FIGURE is a flow chart illustrating the process in which whey is heated then ultrafiltered or microfiltered to produce an α-lactalbumin-enriched fraction.

DETAILED DESCRIPTION OF PREFERRED EMBODIMENTS

For the starting material employed in the present invention, the following types of whey can be used:

i) whey obtained as by-products in the production of cheese, acid casein and rennet casein, and the like, from milk from cows, goats, sheep, etc;

ii) rehydrated whey, obtained by spray drying the whey in (i) above and dissolving the thus obtained powdered whey in water;

or iii) whey protein concentrate (WPC), and the like, prepared from whey, and which contains α-lactalbumin and β-lactoglobulin.

One or more than one of the above whey are mixed and the pH adjusted to 4.0–7.5 before or after the heating process. # However, when the pH is already in the above noted range, it is heated as such, omitting the pH adjustment. The reason for maintaining pH in the above range is to promote a better aggregation of β-lactoglobulin molecules. It has been noted that the pH range which most efficiently promotes aggregation of β-lactoglobulin is at approximately pH 6.0 or 4.5.

The heating of whey should be carried out at a temperature above 80° C., preferably above 85° C., for at least 5 minutes, or alternatively, subject to an ultrahigh temperature pasteurization (UHT) at 100°–120° C., for at least 2 seconds. Obviously, rehydrated whey which has already been heat processed does not require any re-heating.

By heating whey at the above mentioned pH the molecules of β-lactoglobulin in the whey aggregate with themselves or with molecules of other whey proteins, thus increasing their apparent molecular weight, which causes the molecular weight difference with α-lactalbumin to become larger.

The whey which has been heat-processed as above is then passed through an ultrafiltration membrane having a cut-off molecular weight of 50000 Da or higher, or through a microfiltration membrane having a pore size of not larger than 0.5 μm and not smaller than 0.01 μm, to allow α-lactalbumin to pass through the membrane as permeate but β-lactoglobulin is concentrated on the retentate side. In the foregoing membrane process, where the cut-off molecular weight of the ultrafiltration is less than 50000 Da or the pore size of the microfiltration is smaller than 0.01 μm, the production efficiency of α-lactalbumin will be lowered because its molecules may not readily pass through its pores, whereby fractionation of α-lactalbumin and β-lactoglobulin may not be substantially carried out. On the other hand, when the pore size of the microfiltration is larger than 0.5 μm, both β-lactoglobulin, which has increased its apparent molecular weight by heating, and α-lactalbumin molecules will go through the membrane and fractionation of the two substantially may not be performed.

The conditions for processing whey with membranes are the same for ultrafiltration membrane and microfiltration membrane, that is, the process is carried out at not more than 0.5 Mega Pascal for trans-membrane pressure and at least 0.5 meters/second for flow rate on membrane, which results better efficiency in the separation of α-lactalbumin and β-lactoglobulin.

The membrane material of the ultrafiltration membrane and microfiltration membrane employed in the present invention may be either of a high molecular or inorganic material(s). However, where the use of the permeates has to be considered, both from the points of membrane leakage safety and sharper fractionation results, one believes that inorganic membrane materials such as of ceramics are preferable to high molecular membranes.

With the present invention, the whey fraction obtained in the permeate side of the ultrafiltration or microfiltration membrane which has a high α-lactalbumin content as according to the above noted process, can be again subject to ultrafiltration through a membrane having a molecular weight fractionation of smaller than 50000 Da, to separate and recover α-lactalbumin from the retentate side of the membrane, which results in obtaining a further higher concentration of α-lactalbumin.

The accompanying FIGURE is used for further explanation of the process of the present invention. First, the pH of the whey is adjusted to the range of 4.0–7.5 (where the pH of the whey is already within the range, no such adjustment is required). Whey, which has not been heat-processed is taken as the starting material, is heated to a temperature of at least 80° C. as noted above, and then passed through a ultrafiltration or microfiltration with a normal temperature. Where heating the whey has not been undertaken prior to filtration but would be heated simultaneously with the filtration process, the process should be undertaken by ultrafiltration membrane or microfiltration membrane with a high temperature, simultaneously with heating to promote the aggregation of β-lactoglobulin.

Furthermore, where already heat-processed whey, such as rehydrated whey, is used as starting material, ultrafiltration membranes or microfiltration membranes should be employed with a normal temperature. In this case, α-lactalbumin passes through the membrane and results in obtaining a permeate having a high α-lactalbumin content. This permeate normally contains about 0.1% (V/W) of α-lactalbumin, lactose, ash, etc.

The retentate obtained after the membrane operation contains mostly β-lactoglobulin, but some α-lactalbumin is still retained therein. Thus, where a further higher rate of recovery is desirable, some liquid (free from α-lactalbumin) such as water should be added for dilution and subject to diafiltration (DF) which allows the retained α-lactalbumin to pass through, which permeate should then be added to the previously processed permeate obtained by ultrafiltration or microfiltration. Through this operation one may enhance the rate of recovery for α-lactalbumin.

The permeate thus obtained by processing through an ultrafiltration membrane or microfiltration membrane contains milk sugar, ash, water, etc. The permeate may as such be concentrated and removed of lactose by crystallization, and the mother liquor can be used as a composition having a high content of α-lactalbumin. Or, it may further be subject to filtration with an ultrafiltration membrane having a small cut-off molecular weight which does not allow permeation of α-lactalbumin, to fractionate and concentrate α-lactalbumin only.

Since the molecular weight of α-lactalbumin is 14000 Da, the ultrafiltration membrane employed in this instance should have a substantially smaller molecular fraction, for example, not more than 50000 Da.

The fraction having a high content of α-lactalbumin thus obtained can be used as such concentrate or rendered to powder by means of spray drying, freeze-drying, or other known methods. This may be added to infants formula, or the like, and used as a breast-milk substitute, or as a nutritional composition for human or animal use. (See accompanying FIGURE)

According to the invention, with the simple pre-treatment of whey of adjusting pH and heating before membrane filtration, a fraction having a high content of α-lactalbumin can be obtained in an industrial/commercial scale at a reasonable cost and high efficiency.

The fraction having a high content of α-lactalbumin thus obtained can be used as starting materials for infant formula, nutritional compositions for human or animal use, or as components in pharmaceutical preparations, and thus are highly advantageous practically.

EXAMPLES

Working examples are provided below for further description of the invention.

EXAMPLE 1

One hundred kilograms of Cheddar cheese whey at pH 5.8 is pasteurized at 120° C. for 5 seconds with a ultra-high temperature apparatus (UHT) and cooled to 50° C. and processed with an ultrafiltration membrane having a cut-off molecular weight of 150000 DA [membrane material: titania/alumina composite membrane, made by Nippon Gaishi KK]. The conditions of the membrane process were:

Temperature: 50° C.

Trans-membrane Pressure: 0.1 MPa (Mega Pascal)

Flow rate on Membrane: 3 meters/second

Concentration was carried out to a factor of 10, and 90 kg of the permeate and 10 kg of the retentate were obtained.

Table II below gives the percentage contents of the starting whey, of the retentate and of the permeate with respect to protein, α-lactalbumin and β-lactoglobulin; also the ratio of contents of α-lactalbumin/β-lactoglobulin is given as α/β.

As apparent from Table II, the α/β in the whey is 0.38 where the ratio in the permeate after membrane process is 3.95, showing a higher than ten-fold increase.

TABLE II

|  | Whey | Retentate | Permeate |
|---|---|---|---|
| Weights | 100 kg | 10 kg | 90 kg |
| Protein | 0.75% | 6.65% | 0.11% |
| α-lactalbumin | 0.16% | 0.82% | 0.087% |
| β-lactoglobulin | 0.42% | 4.01% | 0.022% |
| α/β | 0.38 | 0.20 | 3.95 |

EXAMPLE 2

Non-desalted Gouda cheese whey powder was dissolved in water to prepare 100 kg of 6 wt.% rehydrized whey. After adjusting its pH to 6.0, it was subjected to ultrafiltration with a membrane having a cut-off molecular weight of 150000 Da [membrane material: titania/alumina composite membrane, made by Nippon Gaishi KK]. The conditions of the filtration process were:

Temperature: 50° C.

Trans-membrane Pressure: 0.2 MPa (Mega Pascal)

Flow rate on Membrane: 3 meters/second

The factor of concentration was carried out to 15, and 93.3 kg of the permeate and 6.7 kg of the retentate were obtained. Table III below gives the percentage contents of the starting whey, of the retentate and of the permeate with respect to protein, α-lactalbumin and β-lactoglobulin; also the ratio of contents of α-lactalbumin/β-lactoglobulin is given as α/β.

The α/β in the whey is 0.44 whereas the ratio in the permeate after membrane process is 4.07, showing a higher than nine fold increase.

TABLE III

|  | Whey | Retentate | Permeate |
|---|---|---|---|
| Weights | 100 kg | 6.7 kg | 93.3 kg |
| Protein | 0.70% | 7.99% | 0.11% |
| α-lactalbumin | 0.16% | 1.54% | 0.061% |
| β-lactoglobulin | 0.36% | 5.17% | 0.015% |
| α/β | 0.44 | 0.29 | 4.07 |

EXAMPLE 3

200 kg of Gouda cheese whey at pH 6.0 was subjected to ultrahigh temperature pasteurization at 120° C. for 5 seconds and then cooled to 20° C. Thereafter, the whey was processed with a microfiltration membrane having a pore size of 0.14 μm [membrane materials: zirconia/carbon]. The conditions of the filtration process were:

Temperature: 50° C.

Trans-membrane Pressure: 0.1 MPa (Mega Pascal)

Flow rate on Membrane: 5 meters/second

Concentration of the retentate was carried out to a factor of 5, added 80 kg of water and then subject to diafiltration to the factor of 2. The resultant permeate was added to the permeate obtained by microfiltration, whereby 240 kg of the permeate and 40 kg of the retentate were obtained.

Table IV below gives the percentage contents of the starting whey, of the retentate and of the permeate with respect to protein, α-lactalbumin and β-lactoglobulin; also the ratio of α-lactalbumin/β-lactoglobulin contents is given as α/β.

The ratio of α/β in the permeate after the filtration process is 6.32, which shows an increase by a factor of 14.3 to the starting whey.

TABLE IV

|  | Whey | Retentate | Permeate |
|---|---|---|---|
| Weights | 200 kg | 40 kg | 240 kg |
| Protein | 0.70% | 2.66% | 0.14% |
| α-lactalbumin | 0.16% | 0.08% | 0.12% |
| β-lactoglobulin | 0.36% | 1.69% | 0.019% |
| α/β | 0.44 | 0.047 | 6.32 |

EXAMPLE 4

The permeate obtained in Example 3 was further subjected to filtration with a ultrafiltration membrane having a cut-off molecular weight of 20000 Da [membrane materials titania/alumina composite membrane made by Nippon Gaishi KK] for the purpose of desalting and removing lactose. The conditions of the filtration process was:

Temperature: 50° C.

Trans-membrane Pressure: 0.3 MPa (Mega Pascal)

Flow rate on Membrane: 5 meters/second

After concentration was carried out to a factor of 6, 80 kg of water was added and subjected to diafiltration (DF), and the concentration carried out to a factor of 2, where by 40 kg of the retentate was obtained. The composition of the retentate in weight % was:

| Total solids | 2.934 |
|---|---|
| Protein | 0.834 |
| α-lactalbumin | 0.72 |
| β-lactoglobulin | 0.114 |
| Sugars | 2.0 |
| Ash | 0.1 |
| pH | 6.0 |

The rate of recovery for α-lactalbumin was 86.9 % based on the starting whey.

EXAMPLE 5

To 706 kg of the desalted retentate obtained in Example 4, 17.8 kg of skim milk powder, 33.3 kg of lactose, and 0.5 kg of vitamins and minerals were dissolved therein; this was further mixed with 27.3 kg of vegetable oil followed by homogenization. The resulting solution was pasteurized and subjected to concentration and drying according to known methods; 100 kg of breast-milk substitute was obtained.

EXAMPLE 6

To 1,439 kg of desalted retentate obtained in Example 4, 17.0 kg of dextrin, 16.0 kg of lactose and 1.4 kg of vitamins and minerals were dissolved therein. Then, 26.8 kg of vegetable oil was mixed thereto followed by homogenization. The resulting solution was pasteurized and subjected to concentration and drying according to known methods. This powdered nutritional composition can be used for feed additives for baby calves and baby pigs.

What is claimed is:

1. A process for preparing an a-lactalbumin-enriched fraction from whey containing α-lactalbumin and β-lactoglobulin comprising the steps of:

(a) once heating whey adjusted to a pH of from about 4.0 to about 7.5 to a temperature of 85° C. or higher for a time sufficient to induce aggregation of the β-lactoglobulin molecules;

(b) simultaneously with or after said heating, once contacting the pH-adjusted whey with a single ultrafiltration membrane having a molecular weight cut-off of above 50,000 daltons, or with a single microfiltration membrane having a pore size of from about 0.01 mm to about 0.5 mm, thereby forming a permeate; and, (c) recovering said fraction from the once-filtered permeate, said fraction having a ratio of α-lactalbumin to β-lactoglobulin greater than 3:1.

2. The process of claim 1 wherein said heating step comprises maintaining the pH-adjusted whey at a temperature of 85° C. or higher for at least 5 minutes.

3. The process of claim 1 wherein said heating step comprises maintaining the pH-adjusted whey at a temperature of from about 100° C. to about 120° C. for at least 2 seconds.

4. The process of claim 1 wherein said single filtration of step (b) is carried out with said ultrafiltration membrane at a transmembrane pressure of not more than 0.5 MPa.

5. The process of claim 1 wherein said single filtration of step (b) is carried out with said microfiltration membrane at a flow rate of at least about 0.5 meters per second.

6. A process for preparing from whey a fraction having a high content of α-lactalbumin comprising the steps of:

(a) once heating whey adjusted to a pH of from about 4.0 to about 7.5, to a temperature of 85° C. or higher;

(b) simultaneously with or after said heating, contacting the pH-adjusted whey with a first ultrafiltration membrane having a molecular weight cut-off of at least about 50,000 Da, or with a first microfiltration membrane having a pore size of from about 0.01 to about 0.5 mm, thereby forming a first permeate containing α-lactalbumin and a retentate;

(c) adding water to the retentate and subjecting the retentate to diafiltration, thereby forming a second permeate containing α-lactalbumin;

(d) combining the first and second permeates; and, (e) recovering said fraction having a α-lactalbumin:β-lactoglobulin ratio of at least 6 from the combined permeates.

7. The process of claim 6 wherein said heating step comprises maintaining the pH-adjusted whey at 85° C. or higher for at least 5 minutes.

8. The process of claim 6 wherein said heating step comprises maintaining the pH-adjusted whey at about 100° to about 120° C. for at least 2 seconds.

9. A process of claim 6 wherein said first filtration step is carried out with said first ultrafiltration membrane at a transmembrane pressure not more than 0.5 MPa.

10. The process of claim 6 wherein said first filtration step is carried out with said microfiltration membrane at a flow rate of at least about 0.5 meters per second.

11. A composition comprising a fraction comprising α-lactalbumin and β-lactoglobulin in a ratio of at least 6 to 1 obtained by the process of claim 6.

12. The composition of claim 11 wherein said composition is a breast-milk substitute.

13. The process of claim 6 further comprising the steps of:

(a) ultrafiltering the combined permeates of step (d) to form a second retentate;

(b) adding water to the second retentate and subjecting the second retentate to diafiltration, thereby forming a third retentate; and, (c) recovering the α-lactalbumin fraction in the third retentate, said fraction having an α-lactalbumin:β-lactoglobulin ratio greater than 6 to 1.

14. A composition comprising a fraction comprising α-lactalbumin and β-lactoglobulin in a ratio greater than 6 to 1 obtained by the process of claim 13.

15. The composition of claim 14 wherein said composition is a breast-milk substitute.

16. The composition of claim 14 wherein said composition is a feed additive for livestock.

* * * * *